(12) United States Patent
Ammann (10) Patent No.: US 7,683,803 B2
(45) Date of Patent: Mar. 23, 2010

(54) SIGNAL TRANSMISSION DEVICE FOR A MEASURING PROBE, AS WELL AS TRANSMISSION METHOD AND MEASURING PROBE

(75) Inventor: Juergen Ammann, Zurich (CH)

(73) Assignee: Mettler-Toledo AG, Greifensee (CH)

( * ) Notice: Subject to any disclaimer, the term of this patent is extended or adjusted under 35 U.S.C. 154(b) by 172 days.

(21) Appl. No.: 12/013,829

(22) Filed: Jan. 14, 2008

(65) Prior Publication Data
US 2008/0165027 A1 Jul. 10, 2008

Related U.S. Application Data

(63) Continuation of application No. PCT/EP2006/064112, filed on Jul. 11, 2006.

(30) Foreign Application Priority Data

Jul. 14, 2005 (EP) .................................. 05106470

(51) Int. Cl.
G08C 19/22 (2006.01)
(52) U.S. Cl. .................. 340/870.07; 324/126; 324/142; 700/195
(58) Field of Classification Search ............ 340/870.07; 324/142, 126; 700/195
See application file for complete search history.

(56) References Cited

U.S. PATENT DOCUMENTS 3,962,697 A 6/1976 Vreeland

| 5,500,879 A * | 3/1996 | Webster et al. ............... 375/353 |
| 7,256,575 B2 * | 8/2007 | Pollock et al. ............... 324/142 |
| 2006/0161359 A1 * | 7/2006 | Lalla ........................... 702/65 |

FOREIGN PATENT DOCUMENTS

| EP | 0 153 437 (A1) | 9/1985 |
| EP | 0 419 769 (A2) | 4/1991 |

(Continued)

OTHER PUBLICATIONS

U. Tietze, Ch. Schenk, Semiconductor Circuit Design, 11th edition, 2nd printing, Springer Publications, Berlin 1999, .Chapter 23, vol. 4, pp. 1256-1259 (cited on page 1 of the present application).

(Continued)

*Primary Examiner*—Timothy Edwards, Jr.
(74) *Attorney, Agent, or Firm*—Buchanan Ingersoll & Rooney PC (57) ABSTRACT

A signal transmission device is disclosed, which serves to connect a measuring probe, in particular a pH measuring probe or an oxygen measuring probe, to a signal-processing unit. The signal transmission device includes a differential amplifier at whose non-inverting input an input signal can be applied which is provided by an electrode of the measuring probe, and from which a corresponding low-impedance output signal can be delivered to a transmission line, by which the output signal can be transmitted to the signal-processing unit. The output of the differential amplifier can be connected via a first resistor to the transmission line and to the inverting input of the differential amplifier, and can be connected to the input of a first control unit by which signals can be registered, such as clock signals and/or data, which are applied to the transmission line by the signal-processing unit.

19 Claims, 6 Drawing Sheets

FOREIGN PATENT DOCUMENTS

EP  0 497 994 (A1)  8/1992
WO  WO 92/21962 (A1)  12/1992

OTHER PUBLICATIONS

Form PCT/ISA/210 (International Search Report) dated Dec. 6, 2006.

European Search Report (with English translation of category of cited documents) dated Nov. 20, 2006.
U. Tietze, "Kapitel 22: Meβschaltungen", 11, Auflage, 1. Nachdruck, Springer Verlag, Berlin, 1999, pp. 1189-1191 ("Chapter 22, Semiconductor Circuit Design", 11th Edition, 2nd Printing, Springer Publications, Berlin, 1999), cited on p. 1 of the present application.
"Process Measurement Solutions Catalog Jun. 2005" Mettler-Toledo GmbH, CH-8902 Urdorf, pp. 24, 25, 66, and 67.

\* cited by examiner

SIGNAL TRANSMISSION DEVICE FOR A MEASURING PROBE, AS WELL AS TRANSMISSION METHOD AND MEASURING PROBE

RELATED APPLICATIONS

This application claims priority under 35 U.S.C. §119 to EP Application 05106470.7 filed in Europe on Jul. 14, 2005, and as a continuation application under 35 U.S.C. §120 to PCT/EP2006/064112 filed as an International Application on Jul. 11, 2006 designating the U.S., the entire contents of which are hereby incorporated by reference in their entireties.

TECHNICAL FIELD

The present disclosure relates to a signal transmission device for a measuring probe, in particular an electrochemical measuring probe such as a pH-measuring probe or an oxygen measuring probe, and it further relates to a transmission method and a measuring probe.

BACKGROUND INFORMATION

According to, U. Tietze, Ch. Schenk, Halbleiterschaltungstechnik, 11. Auflage, 1. Nachdruck, Springer Verlag, Berlin 1999, Kapitel 22, Seiten 1189 und 1190 (*U. Tietze, Ch. Schenk, Semiconductor Circuit Design*, $11^{th}$ edition, $2^{nd}$ printing, Springer Publications, Berlin 1999, Chapter 22, pp. 1189-1190) (hereinafter, "*Tietze*"), it is often desired to first transform measured electrical signals before they are sent for example to an A/D converter in a processing unit. According to *Tietze*, measuring circuits are used which deliver an output signal supplied by a low-impedance voltage source. One way to measure the voltage of a high-impedance signal source without putting a load on the source is to use operational amplifiers as impedance converters. According to *Tietze*, attention is paid to the fact that the high-impedance input conductor line is sensitive to capacitative interference.

According to *Tietze*, Chapter 23.4, pp. 1256-1258, the sensor and the location at which the signals are evaluated are often separated by large distances and areas with high levels of interference. The amplifier that serves to amplify the measured signals, for example the impedance converter shown in *Tietze*, page 1189, FIG. 22.1, is therefore arranged in immediate proximity to the sensor.

According to WO 92/21962, there is a growing trend to use electrode systems, primarily glass electrodes, for the measurement of hydrogen ion concentrations in liquids, i.e. for pH measurements, for example to monitor chemical and biological processes in the field of food processing technology. The increasing use of electrodes for these purposes leads to increasingly stringent requirements in regard to the measurement accuracy in long-term use. Maintaining a satisfactory measurement accuracy can involve continuous monitoring of the condition of the electrodes being used, because the measurement accuracy could become compromised for example as a result of damage to the ion-sensitive membrane, contamination of the diaphragm, interruption of conductors and/or a short circuit within the electrode. The need to eliminate these performance-compromising factors as much as possible has led to a growing demand for methods of failure recognition which allow the condition and the proper functioning of the glass electrode to be monitored without interrupting the process in which the electrode is used and in particular without having to uninstall the glass electrode or to remove it from the medium being measured.

According to WO 92/21962, a measuring probe which includes a glass electrode and a reference electrode and which is immersed in a measurement medium is subjected to a square-wave pulse of variable amplitude and duration from a high-impedance source; the voltage of the measuring probe which has been changed by the probe impedance is measured and the measurement values are compared to a reference value for an intact measuring probe as determined by experiment or calculation. The square-wave pulses in this setup are presented at the analog output of a processor and are delivered to the measuring probe through a separate transmission line.

In a process described in EP 0 419 769 A2, the monitoring is carried out by symmetrical bipolar current pulses which are delivered by a control unit. The period length of the current pulses is freely selectable and can be set in accordance with the accuracy required for testing the probe. This method can involve a relatively extensive amount of circuitry, in particular two control lines which, for the generation of the symmetric bipolar current pulses, allow switching between a positive voltage source and a negative voltage source, or switching between the measurement phase for measuring the pH value and a test phase for testing the electrodes.

A method is disclosed in EP 0 497 994 A1 for testing a pH measuring electrode which in addition to the glass electrode and the reference electrode includes an auxiliary electrode. The disclosed concept further includes two processing devices which are supplied with an AC test voltage by a first and a second generator, respectively. The first generator in this arrangement works at a frequency that is an integer multiple of the frequency of the second generator. This allows separate monitoring of the glass electrode and the reference electrode. In the first case, the resistance of the chain formed of the glass electrode and the auxiliary electrode is tested, while in the second case the resistance of the chain formed of the reference electrode and the auxiliary electrode is tested. With the aforementioned frequency ratio between the generators, it is possible to achieve a sufficiently accurate differentiation between the output signals of the two processing units, as one output signal is suppressed in each case by the phase-sensitive rectification in the processing circuit of the other electrode. The processing devices therefore no longer directly detect the potential difference between the glass electrode and the reference electrode. They detect, however, a difference between the potentials of the glass electrode and the auxiliary electrode, and between the reference electrode and the auxiliary electrode. As both of the differences in potential are referenced to the same potential of the auxiliary electrode, the difference between the potentials of the glass electrode and the reference electrode can be determined by means of a differential amplifier. With this measuring circuit, the measuring probe therefore receives the AC test voltages of two different generators. These AC test voltages, in turn, are used for the subsequent phase-coherent processing of the signals and therefore also have to be transmitted normally from the processing unit to the measuring probe through appropriate conductor lines.

The use of additional conductor lines for the transmission of signals can involve added expense and complexity. Also, systems that are already installed can lack the conductor lines, and can either not be retrofitted or can be retrofitted with added cost and downtime of the system. With the trend towards miniaturization and the possibilities offered thereby for a decentralized arrangement of intelligent components, the desire for transmitting additional signals is on the increase, and more highly developed measuring probes that are designed for decentralized installations may only be of limited use in existing systems.

SUMMARY

A signal transmission device is disclosed for a measuring probe, as are transmission methods and a measuring probe, in particular a pH measuring probe or an oxygen measuring probe, for the signal transmission device.

A signal transmission device is disclosed, comprising a differential amplifier having a non-inverting input for receiving an input signal provided by an electrode of a measuring probe, and having an output configured to deliver a low-impedance output signal via a transmission line to a signal-processing unit, wherein the output of the differential amplifier is connected via a first resistor to the transmission line and to an inverting input of the differential amplifier, and is connected to the input of a first control unit that is operable to register signals such as clock signals and/or data which are applied to the transmission line by the signal-processing unit.

A method for the transmission of signals between a measuring probe and a signal-processing unit is disclosed comprising applying an input signal provided by an electrode of the measuring probe to a differential amplifier non-inverting input to deliver a low-impedance output signal to a transmission line which transmits the output signal to a signal-processing unit, and supplying the output signal of the differential amplifier via a first resistor to the transmission line as well as to the inverting input of the differential amplifier, and supplying the output signal to the input of a first control unit that is operable to register signals applied to the transmission line by the signal-processing unit.

BRIEF DESCRIPTION OF THE DRAWINGS

Exemplary embodiments will be explained in more detail with reference to the drawings, wherein.

DETAILED DESCRIPTION

An exemplary signal transmission device for use with a measuring probe includes a differential amplifier, at whose non-inverting input an input signal can be applied which is provided by an electrode of the measuring probe, and from whose output a corresponding low-impedance output signal can be delivered to a transmission line by which the output signal can be transmitted to a processing unit.

According to an exemplary embodiment, the output of the differential amplifier is connected on the one hand by way of a first resistor to the transmission line as well as to the inverting input of the differential amplifier and on the other hand to the input of a first control unit that is operable to register signals such as clock signals and/or data which are applied to the transmission line by the signal-processing unit.

As described in *Tietze, page* 1189, by using a differential amplifier as an impedance converter, a voltage of a high-impedance voltage source, for example the voltage of a pH-measuring chain immersed in a liquid, can be measured without putting a load on the source. The differential amplifier has a high input resistance and a small output resistance which ensures that the measured signal is passed on to the transmission line with low impedance. If the differential amplifier has an amplification factor of 1, the output voltage delivered to the transmission line can be held exactly at the level of the measured input voltage, independent of the load presented by the processing unit at the receiving end. If voltages are applied to the transmission line with relatively high impedance for example by the processing unit, this can be corrected immediately by the differential amplifier by changing the output current. In known circuit arrangements of this kind, signals were transmitted in unidirectional mode through the transmission line from the measuring probe to the processing unit, while the transmission of signals from the processing unit to the measuring probe took place through different lines.

Exemplary embodiments disclosed herein allow bidirectional transmission of signals through a transmission line that is connected by way of a first resistor to a low-impedance output of a differential amplifier. Due to the additional connection of the transmission line to an inverting input of the differential amplifier, the voltage in the transmission line can be exactly at the level of the input voltage multiplied by the amplification factor. If the transmission line and the inverting input of the differential amplifier are short-circuited to each other, the output voltage in the transmission line can equal exactly the load-free input voltage which is present at the non-inverting input of the differential amplifier, whereby a precise measurement of the physical quantities can be assured which are the object of the measurements to be performed with the measuring probe.

Voltages that are imposed on the transmission line or currents that are directed into the transmission line can be immediately compensated by the differential amplifier through a change of the potential at the output of the differential amplifier, so that currents which as a result are entering the transmission line are drained away through the first resistor and the internal resistance of the differential amplifier. Voltages which are imposed on the transmission line therefore can cause proportional voltage changes to occur at the output of the differential amplifier and thus at the input of the first control unit. Although the voltage in the transmission line is kept constant at the level of the measured signal, it is therefore possible to transmit signals from the processing unit to the measuring probe through the transmission line.

The monitoring of a pH measuring probe for example in the method described in EP 0 419 769 A2 is performed by symmetric bipolar current pulses which are produced by a control unit. The evaluation of the resultant signal profiles can take place in the processing unit in a phase-coherent manner. It is therefore possible according to exemplary embodiments disclosed herein that clock signals are entered by the processing unit into the transmission line and received by the first control unit and that bipolar current pulses are formed which are timed in accordance with the clock signals.

To carry out this feature, a signal source which is provided in the processing unit and serves in particular for the delivery of data or clock signals is connected to the transmission line through a second resistor Via the signals put out by this signal source, the first control unit which is part of the measuring probe and a second control unit which is part of the processing unit can be synchronized with each other. It is further possible that the signal source is controlled by the second control unit dependent on the data and/or clock signals that are to be transmitted. As a substitute for the signal source, a controllable switch can be provided whereby the resistor connected to the transmission line, or a voltage divider, can be connected to a specific potential, for example to ground potential.

The clock signals and/or data delivered by the signal source to the transmission line are regenerated in the first control unit. For example, the bipolar current pulses of test signals described in EP 0 419 769 A2 or EP 0 497 994 A1, such as symmetrical square-wave signals of a first or a further frequency $f_G$, $f_R$ or further kinds of signals such as sinusoidal signals or triangular signals are derived from said clock signals and/or data and are transmitted to at least one electrode of the measuring probe. The resultant time profiles of the voltages at the electrode or electrodes are transmitted by way of at least one differential amplifier and at least one transmission line to the second control unit where they are evaluated.

If each electrode of a measuring probe is to be monitored individually, one could provide several identical signal transmission devices. In this case it is sufficient to use only one control unit in the measuring probe, as the test signals for the electrodes are produced on the basis of the signals that are transmitted through only one transmission line. If test signals of different frequencies $f_G$, $f_R$ are used for the electrodes, as described in EP 0 497 994 A1, clock signals are transmitted for the first frequency $f_G$, and the additional frequencies $f_R$, ... are derived from the first frequency for example by means of a frequency divider.

Given that in current applications only a small volume of data and clock signals are transmitted, time windows can be provided in the first and/or the second control unit within which data or clock signals can be received. Outside of these time windows the control units are locked, so that interference factors are suppressed. The time windows can be formed dependent on the polarity and/or the frequency of the signals being transmitted and, if applicable, dependent on the transmission protocol being used. If for example a pulse of positive polarity is expected, pulses of negative polarity will be ignored. It is further possible that parcels of data are transmitted periodically at larger time intervals and are received in commensurate time windows. Microprocessors can be employed in the control units. Because of the capabilities of microprocessors it is therefore possible to perform a multitude of operations in the measuring probe. For example, cyclic load exposures of the measuring probe can be registered and interrogated by the processing unit.

For example, differential amplifiers can be configured as operational amplifiers with voltage input and voltage output or operational amplifiers with current input and voltage output (trans-impedance amplifiers).

The signal transmission device and the method disclosed herein can be used for any sensors or measuring probes desired, such as pH measuring probes or oxygen measuring probes of the kinds described in "Process Measurement Solutions Catalog 2005/06", Mettler-Toledo GmbH, CH-8902 Urdorf, on pages 24, 25 and 66, 67.

Thus, if signal transmission devices as disclosed herein are used in conjunction with conventional signal lines for the bidirectional transmission of signals in order to realize additional functionalities, it is possible to expand existing systems without the need for additional installations.

Figure 1:
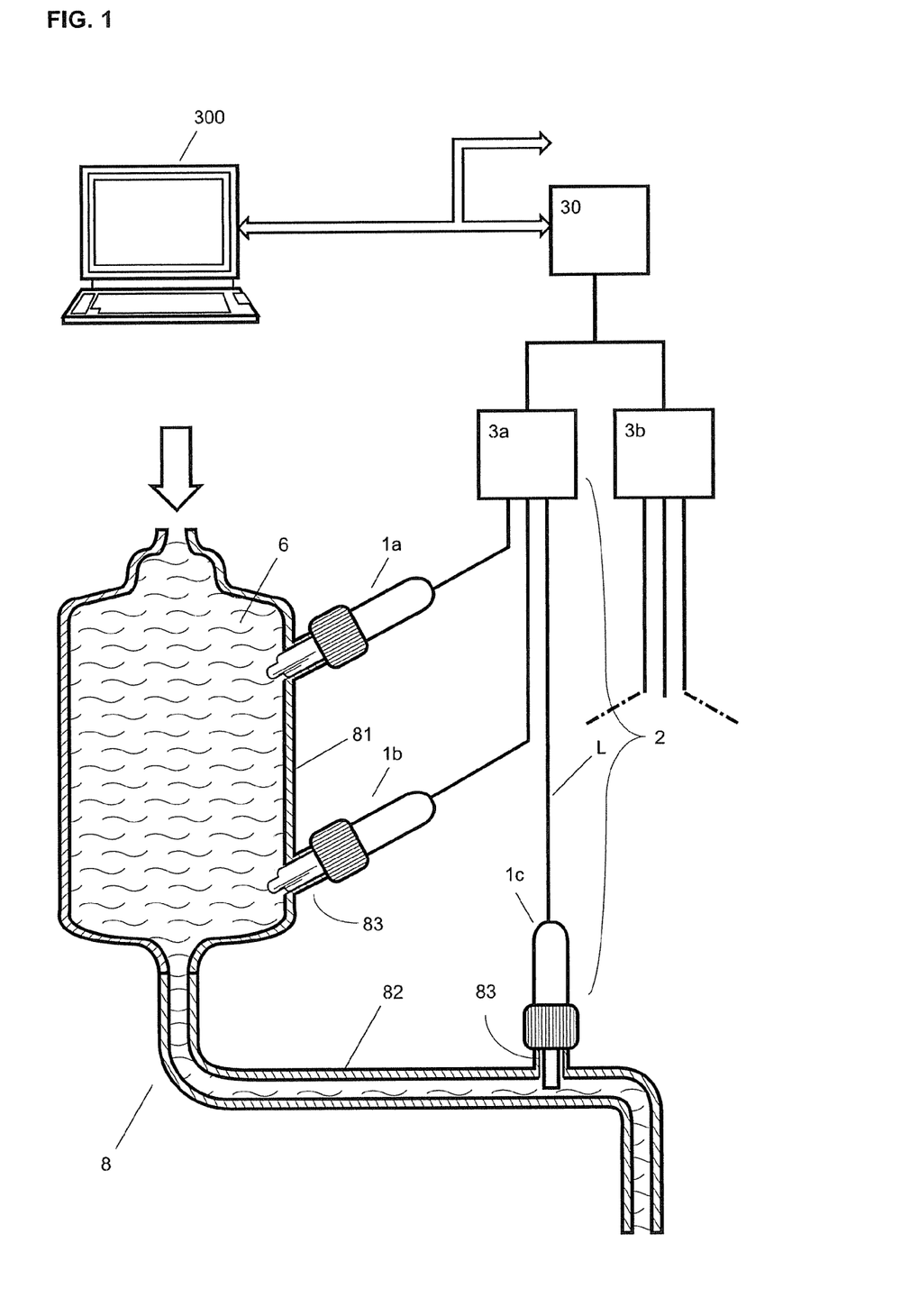
FIG. 1 represents an exemplary single-stage system operating according to the disclosure, with a container 8, 81, 82 in which three measuring probes 1a, 1b, 1c are incorporated which are connected to a lead computer 300 through measurement converters or signal-processing units 3a, 3b, a segment coupler 30 and a bus system.

FIG. 1 illustrates a system with a container arrangement 8 consisting of (e.g., comprising) a container 81 filled with a process material 6, which could be connected through a connecting pipeline 82 to a system unit of a next-following process stage. The properties of the process material 6 are measured by means of measuring probes 1a, 1b, 1c which are connected by way of signal transmission devices 2 according to an exemplary embodiment to a signal-processing unit 3a or 3b. The signal-processing units 3a, 3b which among other functions serve as measurement converters are connected to a lead computer 300 by way of a segment coupler 30.

Figure 2:
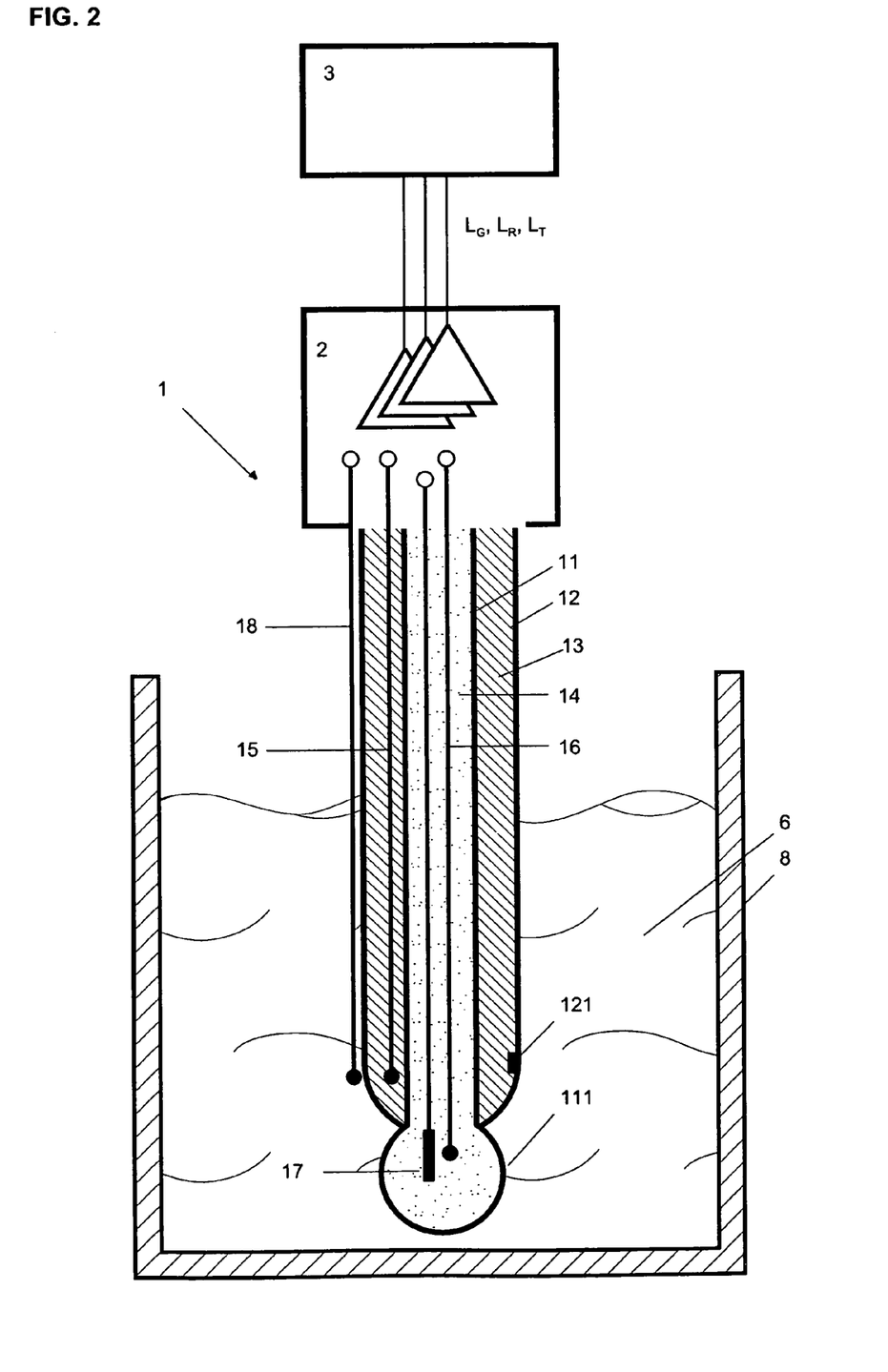
FIG. 2 schematically represents an exemplary measuring probe 1 immersed in a test liquid 6 and connected to a signal-processing unit 3 by an exemplary signal-transmission device 2 according to the disclosure.

An exemplary principal structure of a pH measuring probe which is configured as a single rod measuring chain comprising a glass electrode 16, a reference electrode 15 and an auxiliary electrode 18 is schematically illustrated in FIG. 2. The glass electrode which includes a conductor element 16 and the reference electrode which contains a reference element 15 are structurally combined in the measuring probe 1. In a first chamber inside an interior tube 11 and an adjoining thin-walled glass hemisphere or glass membrane 111, the conductor element 16 is immersed in a solution of defined pH value or an interior buffer 14 which establishes the conductive connection between the inside of the glass membrane 111 and the conductor element 16. The voltage potential which sets itself up on the conductor element 16 during the measurement (see FIG. 5, signal source $SQ1_G$) is compared to the voltage potential of a reference element 15 (see FIG. 5, signal source $SQ1_R$), which is immersed inside an exterior tube 12 in an electrolyte or an exterior buffer 13 which passes by slow diffusion through a porous separating wall or diaphragm 121 into the test material 6.

Arranged in the interior buffer space is a temperature-measuring sensor 17, through which an automatic compensation of temperature influences and the measurement of temperature cycles can be realized.

An exemplary signal transmission device 2, which is described below in more detail, is incorporated in the head of the measuring probe 1 and connected through signal lines $L_G$, $L_R$, $L_T$ to the signal-processing unit 3.

Figure 3:
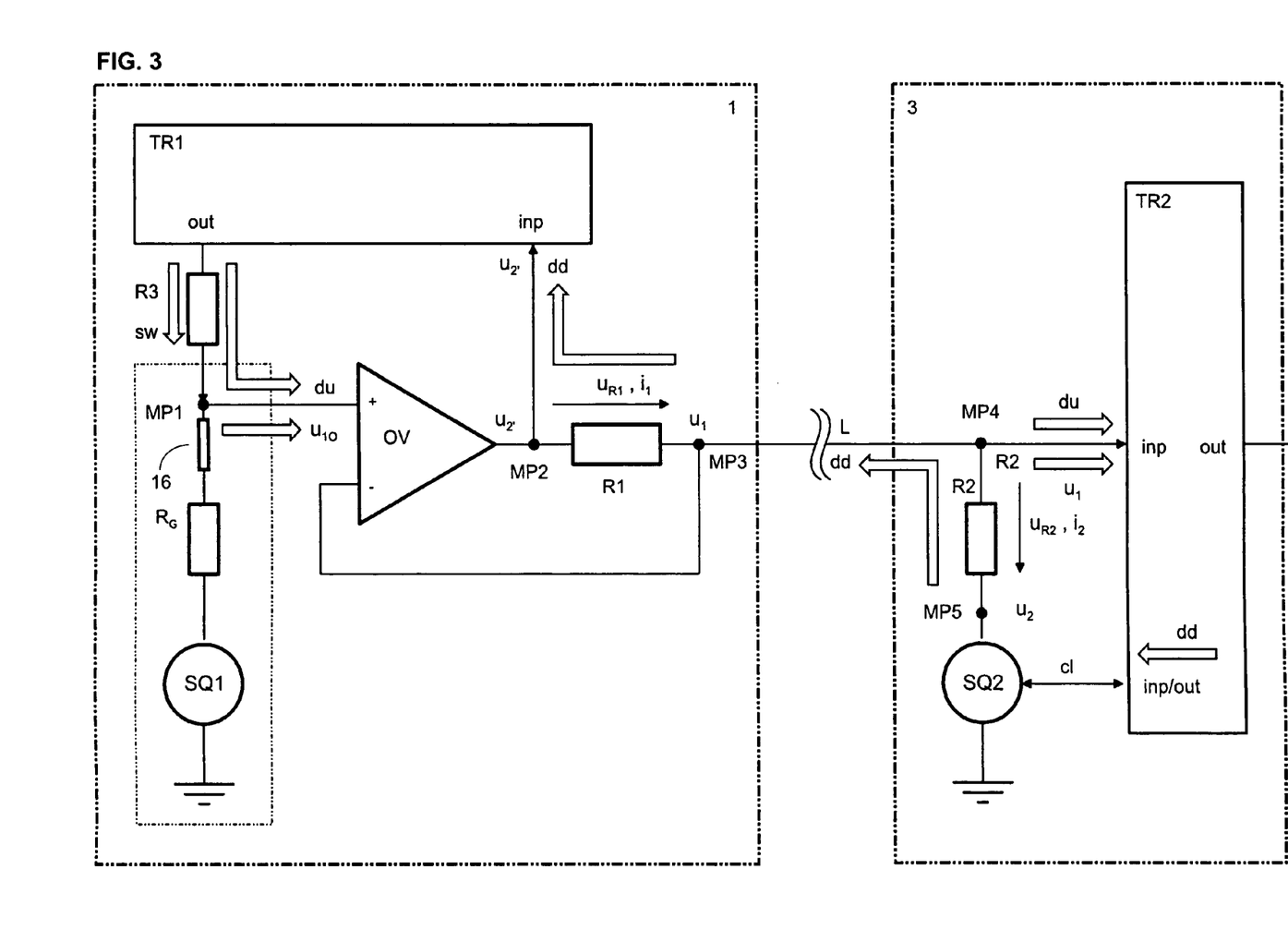
FIG. 3 illustrates a circuit principle of an exemplary signal-transmission device according to the disclosure with an operational amplifier arranged to work as an impedance converter, whose non-inverting input is connected to an electrode of the measuring probe 1 and whose output is connected by way of a first resistor R1 to a transmission line L which is connected to a signal source SQ2 in the processing unit.

FIG. 3 shows an exemplary signal transmission device which is incorporated in a measuring probe 1, with a differential amplifier OV whose non-inverting input receives an input signal $u_{10}$ generated by a glass electrode 16 (see measurement point MP1) and from which a corresponding output signal $u_1$ can be delivered with low impedance to a transmission line L, by which the output signal $u_1$ is transmitted to a signal-processing unit 3. The voltage $u_{10}$ is the aforementioned voltage potential which occurs at the glass electrode 16 as soon as the latter is immersed in the test material. The test material 6 and the glass membrane 111 in this case form a voltage source SQ1 whose internal impedance is determined primarily by the resistance $R_G$ of the glass membrane 111.

The output of the differential amplifier OV (see measurement point MP2) where the voltage $u_2$, is present is connected through a first resistor R1 to the transmission line L as well as to the inverting input of the differential amplifier OV (see measurement point MP3). Since the voltage difference at the inputs of the differential amplifier is practically zero, the voltage $u_1$ at the measurement point MP3 exactly follows the input voltage $u_{10}$ that is present at the non-inverting input of the differential amplifier OV and at the measurement point MP1. The voltage $u_1$ at the measurement point MP3 is held at the same level as the voltage $u_{10}$ at the measurement point MP1 even in the case when a voltage is applied in the signal-processing unit 3 to the transmission line through a second resistor R2. This has the consequence that the current $i_2$ flowing through the second resistor R2 always has to be equal to the current $i_1$ flowing through the first resistor R1. Under the condition that the signal source SQ2 delivers the voltage $u_2$ through the resistor R2 to the transmission line L and that the transmission line L carries no other load, the following equations apply:

$$i_1 = i_2$$

$$u_{R1}/R1 = u_{R2}/R2$$

$$(u_2 - u_1)/R1 = (u_1 - u_2)/R2$$

The voltage u2' which is present at the output of the differential amplifier therefore conforms to the equation:

$$u_{2'} = (u_1 - u_2)R1/R2 + u_1$$

If the values of the resistors R1 and R2 are equal, the following equations apply:

$$u_{2'} = (u_1 - u_2) + u_1$$

$$u_{2'} = 2u_1 - u_2$$

Thus, the voltage $u_1$ (also $u_{10}$) is present at the output of the differential amplifier OV and at the measurement point MP2, on which the voltage difference ($u_1 - u_2$) is superimposed. This voltage $u_{2'}$ is transmitted to the input of a control unit TR1 arranged in the measuring probe 1, which has the capability to produce in a simple manner a signal that is proportional to the voltage $u_2$ and to derive further signals from it or, if data were transmitted, to evaluate them.

Figure 4:
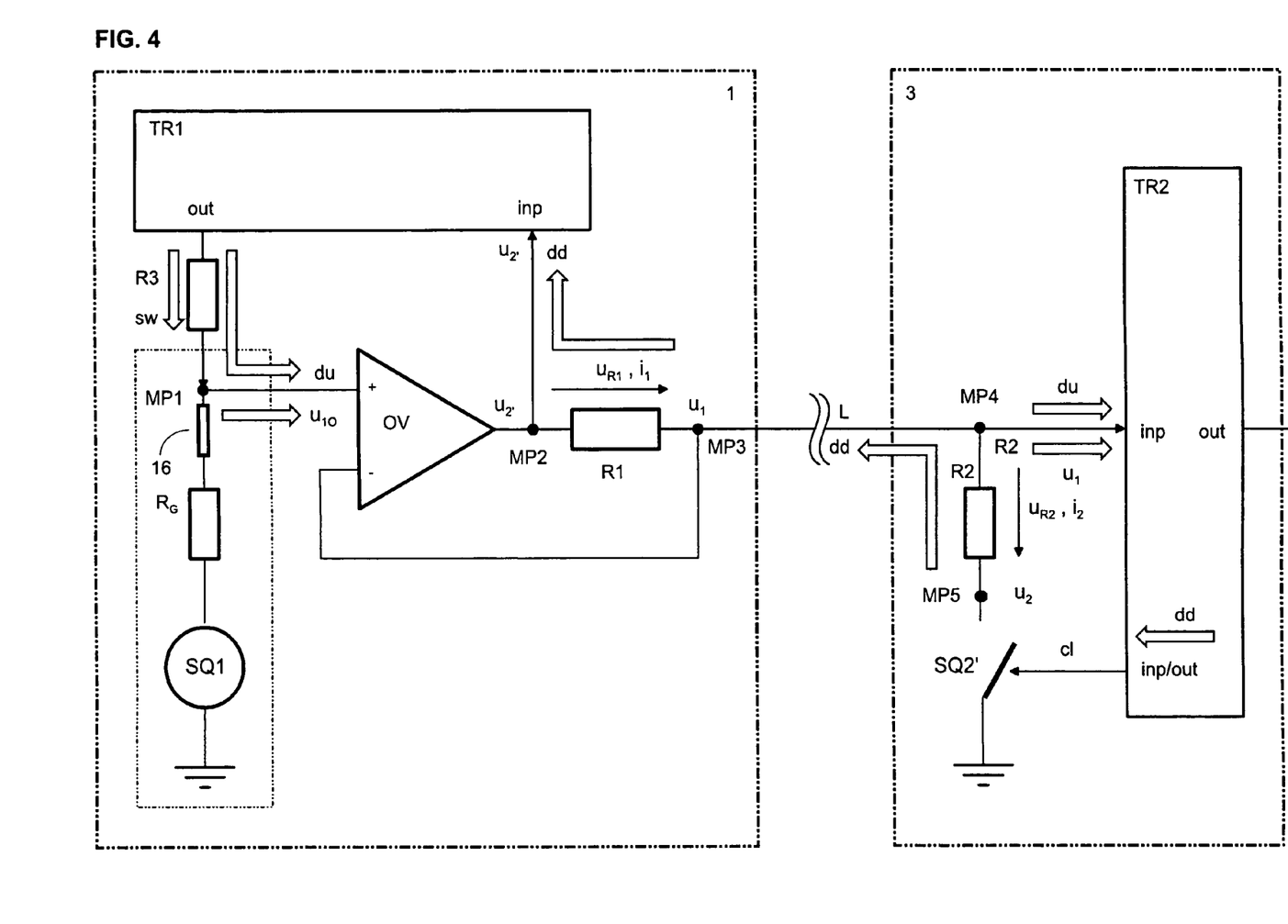
FIG. 4 shows the exemplary signal transmission device of FIG. 3 with a switch serving as a controlled signal source SQ2' which, when closed, connects the transmission line L to ground potential by way of a second resistor R2.

As shown in FIG. 4, the voltage $u_2$ at the measurement point MP5 can of course also be set by a controlled switch SQ2' to a defined potential, for example ground potential, in which case the voltage $u_{2'}$ at the output of the differential amplifier OV, i.e. at the measurement point MP2, takes on the following value:

$$u_{2'} = (u_1 - 0)R1/R2 + u_1$$

$$u_{2'} = u_1(R1/R2) + u_1$$

$$u_{2'} = u_1((R1/R2) + 1)$$

If the switch is in the open position, $u_1 = u_2$, and thus:

$$u_{2'} = (u_1 - u_1)R1/R2 + u_1$$

$$u_{2'} = u_1$$

By operating the switch SQ2', the voltage $u_{2'}$ is therefore switched from one to the other of two values, whereby clock pulses or data can be transmitted from the processing unit 3 or from the second control unit TR2 to the measuring probe 1 or to the first control unit TR1. However, if only one switch SQ2' is used, only unipolar signals can be transmitted, so that if bipolar signals are required, they will have to be derived from the unipolar signals in the first control unit TR1. The clock signals and/or data generated by the switch SQ2' are registered by means of the first control unit TR1, possibly regenerated, and processed.

It is therefore possible, as described in EP 0 419 769 A2 and EP 0 497 994 A1, to transmit test signals sw, for example, in the form of bipolar symmetric square-wave signals from the output of the first control unit TR1 through a third, for example, complex impedance element R3, to the electrode 16, i.e. to the measurement point MP1. It is also possible to superimpose data on the input signal $u_{10}$, for example at periodic intervals and within short time windows, and to have the second control unit TR2 separate the data from the measurement signal. As indicated by arrows in FIG. 4, data dd are transmitted from the processing unit 3 to the measuring probe 1 and data du are transmitted from the measuring probe 1 to the processing unit 3.

Figure 5:
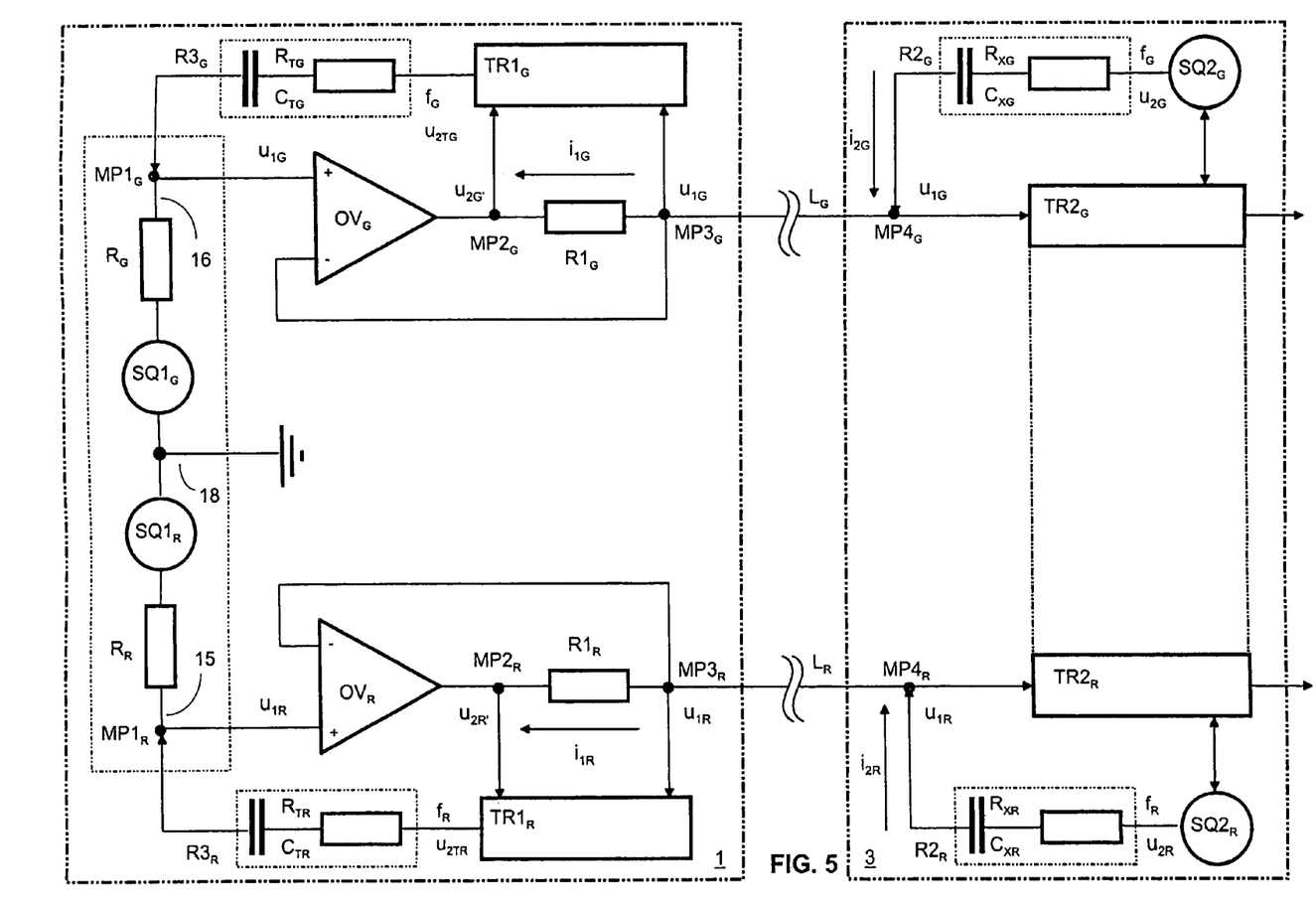
FIG. 5 represents an exemplary signal transmission device with two signal paths serving for the bidirectional transmission of signals.

FIG. 5 shows an exemplary signal transmission device with two signal paths whose design structure is practically identical to the circuit arrangement in FIG. 3, wherein each signal path serves for bidirectional signal transmission and the signal paths are connected to electrodes 15 and 16, respectively, for example to a glass electrode and a reference electrode of the measuring probe 1. The signal paths are provided, respectively, with a first control units $TR1_G$, $TR1_R$ by which the clock signals and/or data delivered by the processing unit 3, specifically by the control units $TR2_G$, $TR2_R$ that are located in the processing unit 3, are registered and processed. Test signals $f_G$, $f_R$ of different frequencies are sent from the two first control units $TR1_G$, $TR1_R$ by way of complex impedance elements $R3_G$, $R3_R$, specifically RC-elements $R_{TG}$, $C_{TG}$ and $R_{TR}$, $C_{TR}$, to the electrodes 15, 16, as described in EP 0 497 994 A1. Signals originating from the signal sources $SQ2_G$, $SQ2_R$ provided in the processing unit 3 are likewise sent by way of complex impedance elements $R2_G$, $R2_R$, specifically RC-elements $R_{XG}$, $C_{XG}$ and $R_{XR}$, $C_{XR}$, to the respective associated transmission lines $L_G$, $L_R$.

Figure 6:
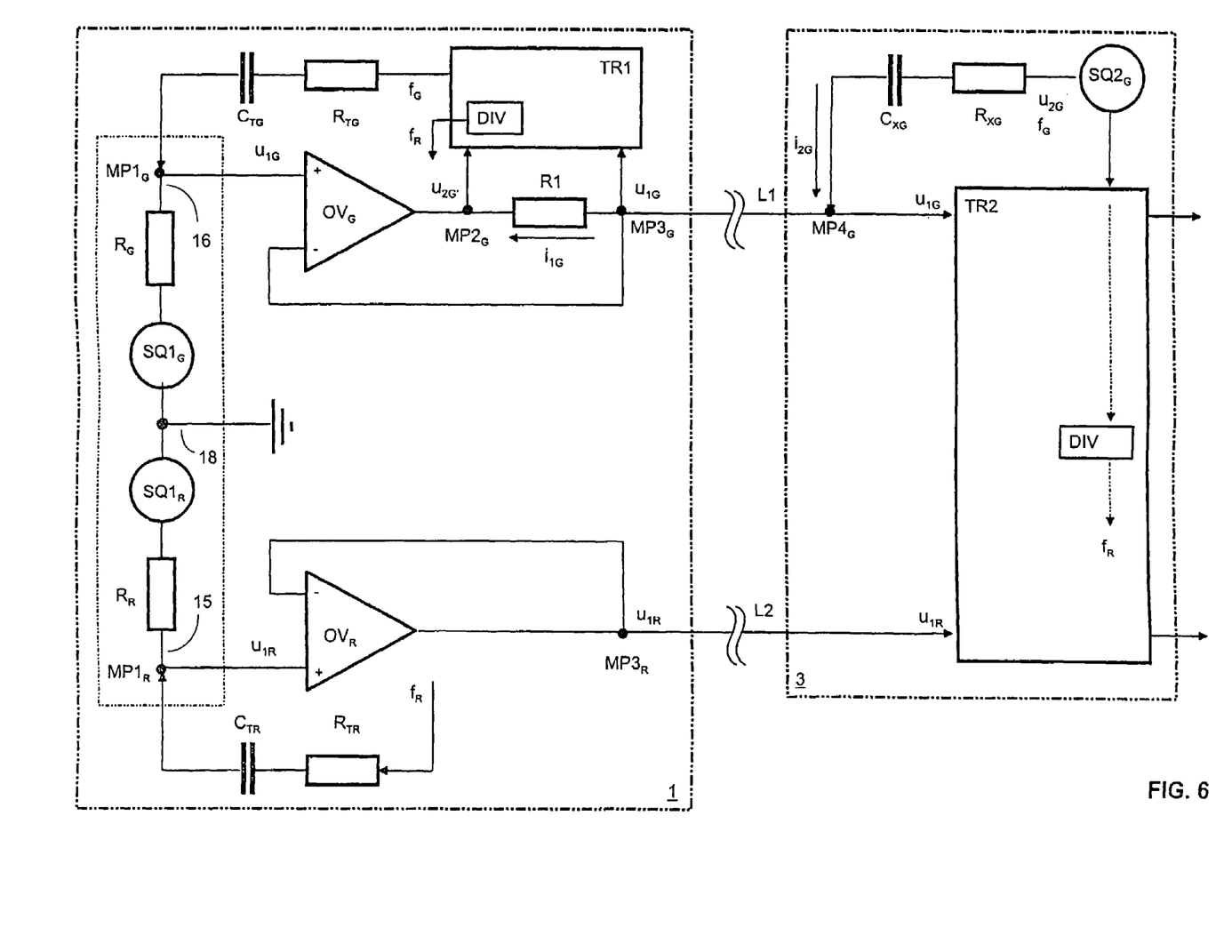
FIG. 6 represents an exemplary signal transmission device with two signal paths, only one of which serves for bidirectional transmission of signals.

FIG. 6 illustrates an exemplary signal transmission device with two signal paths, only one of which serves for bidirectional signal transmission. The test signals and clock signals for the second signal path are generated by means of a frequency divider DIV, whereby the circuit arrangement is considerably reduced in scope. With this arrangement, a first frequency $f_G$ is used to derive a second frequency which can be higher than $f_G$ by an integer multiple, wherein with a divisor <1, $f_G$ is smaller than $f_R$ and with a divisor >1, $f_G$ is larger than $f_R$. Of course, it is also possible to realize the bidirectional signal transmission on the second or a further signal path.

The signal transmission device which has been described in exemplary embodiments can be used for the transmission of data and signals under arbitrarily selected protocols. By using microprocessors in the first and second control units TR1, TR2, it is possible to transmit volumes of data which will also be adequate for applications that may be realized in the future.

Essential elements of the signal transmission device can be incorporated in the measuring probe, so that measuring probes 1 according to the disclosure can be installed in existing systems in place of conventional measuring probes.

It should further be noted that the signal transmission device disclosed herein can be used for any measuring probes and sensors which deliver a current or a voltage representing a measured quantity. Depending on the signal, one of the differential amplifiers or operational amplifiers can be selected from among those presented in *Tietze, page 482*.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. Signal transmission device, comprising
  a differential amplifier having a non-inverting input for receiving an input signal provided by an electrode of a measuring probe, and having an output configured to deliver a low-impedance output signal via a transmission line to a signal-processing unit, wherein the output of the differential amplifier is connected via a first resistor to the transmission line and to an inverting input of the differential amplifier, and is connected to the input of a first control unit that is operable to register signals applied to the transmission line by the signal-processing unit.

2. Signal transmission device according to claim 1, wherein the differential amplifier is an operational amplifier with voltage input and voltage output or a trans-impedance amplifier with current input and voltage output.

3. Signal-transmission device according to claim 1, wherein the differential amplifier is arranged to operate as an impedance converter.

4. Signal-transmission device according to claim 1, wherein a signal source in the signal-processing unit serves to deliver data or clock signals via a second resistor to the transmission line,
and/or wherein a signal source in the signal-processing unit, connected via a second resistor to the transmission line and via a control line to a second control unit in the signal-processing unit, that serves for processing signals and/or data transmitted from the measuring probe, and that is supplied with clock signals from the signal source or transmits data and/or clock signals to the signal source.

5. Signal transmission device according to claim 4, wherein the clock signals and/or data delivered by the signal source into the transmission line are regenerated in the first control unit and test signals derived from them, are applied to at least one electrode of the measuring probe, whereupon resulting profiles of voltages occurring at the electrode are transmitted via at least one differential amplifier and at least one transmission line to the second control unit.

6. Signal transmission device according to claim 5, wherein the signals delivered by at least one electrode are transmitted to the signal-processing unit via respective associated differential amplifiers arranged as impedance converters and via respective associated transmission lines, wherein clock signals and/or data are transmitted through at least one of the transmission lines and can be regenerated by a first control unit which comprises a frequency divider by which test signals for the electrodes can be regenerated.

7. Signal transmission device according to claim 5, wherein the second resistor which connects the signal source to the transmission line, and a third resistor which connects at least one first control unit to an associated electrode, are formed as complex impedance elements.

8. Method for the transmission of signals between a measuring probe and a signal-processing unit comprising:
applying an input signal provided by an electrode of the measuring probe to a differential amplifier non-inverting input to deliver a low-impedance output signal to a transmission line which transmits the output signal to a signal-processing unit; and
supplying the output signal of the differential amplifier via a first resistor to the transmission line as well as to the inverting input of the differential amplifier, and supplying the output signal to the input of a first control unit that is operable to register signals applied to the transmission line by the signal-processing unit.

9. Method according to claim 8, wherein a signal source in the signal-processing unit transmits via a second resistor, data or clock signals, to the transmission line and/or the signal source present in the signal-processing unit sends clock signals via a second resistor to the transmission line and via a control line to a second control unit.

10. Method according to claim 8, wherein clock signals and/or data transmitted through the transmission line are regenerated in the first control unit and test signals derived from them, obtained by subdividing the frequency, are applied to at least one electrode of the measuring probe, whereupon resultant profiles of voltages at the electrode are transmitted to the second control unit via at least one differential amplifier and at least one transmission line to the second control unit where they are evaluated.

11. Method according to claim 8, wherein time windows in which the data and/or clock signals are expected to arrive are formed in the first and/or the second control unit.

12. Signal-transmission device according to claim 2, wherein the differential amplifier is arranged to operate as an impedance converter.

13. Signal-transmission device according to claim 12, wherein a signal source in the signal-processing unit serves to deliver data or clock signals via a second resistor to the transmission line,
and/or wherein a signal source in the signal-processing unit, connected via a second resistor to the transmission line and via a control line to a second control unit in the signal-processing unit, serves for processing signals and/or data transmitted from the measuring probe, and is supplied with clock signals from the signal source or transmits data and/or clock signals to the signal source.

14. Signal transmission device of claim 5, wherein the test signals are square wave signals of a first frequency or a further frequency.

15. Signal transmission device of claim 7, wherein the complex impedance elements are RC elements with a resistor and a capacitor.

16. Method according to claim 9, wherein clock signals and/or data transmitted through the transmission line are regenerated in the first control unit and test signals derived from them, obtained by subdividing the frequency, are applied to at least one electrode of the measuring probe, whereupon resultant profiles of voltages at the electrode are transmitted to the second control unit via at least one differential amplifier and at least one transmission line to the second control unit where they are evaluated.

17. Method according to claim 9, wherein time windows in which the data and/or clock signals are expected to arrive are formed in the first and/or the second control unit dependent on the polarity and/or the frequency of the signals being transmitted, and/or on the transmission protocol being used.

18. A measuring probe for measuring at least one of pH and oxygen, having a signal transmission device comprising:
a differential amplifier having a non-inverting input for receiving an input signal provided by an electrode of a measuring probe, and having an output configured to deliver a low-impedance output signal via a transmission line to a signal-processing unit, wherein the output of the differential amplifier is connected via a first resistor to the transmission line and to an inverting input of the differential amplifier, and is connected to the input of a first control unit that is operable to register signals applied to the transmission line by the signal-processing unit.

19. Method according to claim 11, wherein time windows are formed dependent on polarity and/or frequency of signals being transmitted, and/or on a transmission protocol being used.

* * * * *